(12) United States Patent
Agrawal et al.

(10) Patent No.: US 11,507,169 B2
(45) Date of Patent: Nov. 22, 2022

(54) USER STATE-BASED DEVICE POWER CONSERVATION

(71) Applicant: Motorola Mobility LLC, Chicago, IL (US)

(72) Inventors: Amit Kumar Agrawal, Bangalore (IN); Rachid Alameh, Crystal Lake, IL (US); Jyothsna Bandameedipalli, Bangalore (IN)

(73) Assignee: Motorola Mobility LLC, Chicago, IL (US)

( * ) Notice: Subject to any disclaimer, the term of this patent is extended or adjusted under 35 U.S.C. 154(b) by 126 days.

(21) Appl. No.: 16/375,673

(22) Filed: Apr. 4, 2019

(65) Prior Publication Data

US 2020/0319691 A1    Oct. 8, 2020

(51) Int. Cl.
*G06F 1/3206* (2019.01)
*G06F 1/3287* (2019.01)
*A61B 5/00* (2006.01)
*H04W 52/02* (2009.01)

(52) U.S. Cl.
CPC .......... *G06F 1/3206* (2013.01); *A61B 5/4812* (2013.01); *G06F 1/3287* (2013.01); *H04W 52/028* (2013.01)

(58) Field of Classification Search
CPC ...... G06F 1/3206; G06F 1/3287; G06F 3/015; H04W 25/028; H04M 2250/60; H04M 2250/12; G09G 2330/02
USPC ................................................. 713/320, 323
See application file for complete search history.

(56) References Cited

U.S. PATENT DOCUMENTS

| | | | |
|---|---|---|---|
| 7,010,710 B2* | 3/2006 | Piazza | G06F 1/3231 713/323 |
| 9,094,539 B1* | 7/2015 | Noble | H04M 1/72569 |
| 9,149,599 B2 | 10/2015 | Walter et al. | |
| 9,740,285 B2* | 8/2017 | Beaty | G06F 3/015 |
| 10,657,968 B1* | 5/2020 | Raman | H04N 21/4854 |
| 10,667,007 B2* | 5/2020 | Robinson | H04N 21/4334 |
| 10,762,928 B1* | 9/2020 | Camus | H04N 21/42201 |
| 2010/0098231 A1 | 4/2010 | Wohlert | |
| 2011/0015469 A1 | 1/2011 | Walter et al. | |
| 2012/0254909 A1* | 10/2012 | Serdiuk | H04N 21/443 725/12 |
| 2013/0135108 A1 | 5/2013 | Alameh et al. | |
| 2013/0177883 A1 | 7/2013 | Barnehama et al. | |
| 2013/0283530 A1* | 10/2013 | Main | A47C 27/083 5/600 |

(Continued)

OTHER PUBLICATIONS

Wikipedia, "Rapid eye movement", Feb. 23, 2018 (via wayback machine at http://web.archive.org/web/20180223182501/https://en.wikipedia.org/wiki/Rapid_eye_movement_sleep). (Year: 2018).*

(Continued)

*Primary Examiner* — Paul Yen

(57) ABSTRACT

Systems and methods for managing power and data usage in a mobile electronic communications device entail detecting a sleep state of a user of the device, and entering an idle mode when the sleep state of the user is deep sleep, wherein the idle mode restricts device CPU and network activities to exclude user-centric operations. When the sleep state of the user changes from the deep sleep state, the device exits the idle mode and enters an operative state to execute any pending user-centric operations.

20 Claims, 6 Drawing Sheets

(56) References Cited

U.S. PATENT DOCUMENTS

| | | | |
|---|---|---|---|
| 2014/0101611 A1 | 4/2014 | Lang et al. | |
| 2014/0108842 A1* | 4/2014 | Frank | G06F 1/3234 713/323 |
| 2014/0242559 A1 | 8/2014 | Patel et al. | |
| 2014/0248383 A1* | 9/2014 | Urade | A61K 36/63 424/770 |
| 2015/0208205 A1* | 7/2015 | Chan | H04L 67/1095 709/217 |
| 2016/0311440 A1 | 10/2016 | Gan | |
| 2017/0360362 A1* | 12/2017 | Zhang | A61B 5/7264 |
| 2018/0020424 A1 | 1/2018 | Almalki | |
| 2019/0045046 A1 | 2/2019 | Ma | |
| 2019/0124032 A1 | 4/2019 | Ganesh et al. | |
| 2019/0213060 A1* | 7/2019 | Raymann | G08B 5/222 |
| 2020/0319691 A1 | 10/2020 | Kumar et al. | |

OTHER PUBLICATIONS

Blaise, Malina, "NonFinal Office Action", U.S. Appl. No. 16/375,616, filed Apr. 4, 2019; dated Jun. 29, 2021.

"How Sleep Cycle Works", Sleep Cycle online manual; provided at https://www.sleepcycle.com/how-sleep-cycle-works/ ; Unknown exact publication date but believed to be prior to filing of present application; Viewed online Apr. 20, 2021.

"Kickstarter—Neuroon Open Sleep Tracker", Kickstarter Campaign for Neuroon Sleep Mask; https://www.kickstarter.com/projects/intelclinic/neuroon-open-smartest-sleep-dreams-and-meditation/description ; Open as early as Jul. 24, 2017; Viewed online Apr. 20, 2021.

"LUUNA: Smart Real-Time Music Creating Sleep Mask", Indiegogo.com; Fundraising Source; https://www.indiegogo.com/projects/luuna-smart-real-time-music-creating-sleep-mask#/ ; Launched online Apr. 25, 2018; Viewed online Apr. 20, 2021.

"Philips SmartSleep", Product SmartSleep—Philips USA; Viewed online Apr. 20, 2021 at https://www.usa.philips.com/c-e/smartsleep.html.

"Sleep Shepherd—How Does it Work?", Device Product Page; https://sleepshepherd.com/science/ ; Viewed online Apr. 20, 2021; Unknown exact publication date but believed to be prior to filing of present application.

"Ultimate Brain Power App", Viewed online Apr. 20, 2021 at https://apps.apple.com/us/app/ultimate-brain-power-the-sleep-learning-system/id940983738.

"UserVoice—Pillow", User's Comments; Forum no longer available; Inventor review prior to filing of present application; Comments provided on document submitted labeled MM920180034—Inventor Provided Prior Art—Pillow User Voice.

"Wikipedia—Sleep-learning", Accessed online at https://en.wikipedia.org/wiki/Sleep-learning on Apr. 20, 2021; Last updated Dec. 4, 2020.

Allen, Jennifer, "The 10 Best Apps to Help you Get a Good Night's Sleep", Published online Jun. 28, 2017 at Paste https://www.pastemagazine.com/tech/apps/the-10-best-apps-to-help-you-get-a-good-nights-sle/ ; Viewed online Apr. 20, 2021.

Belluck, Pam, "Sounds During Sleep Aid Memory, Study Find", NY Times Article; Published online Nov. 19, 2009 at https://www.nytimes.com/2009/11/20/science/20sleep.html ; Viewed online Apr. 20, 2021.

Blaise, Malina, "Final Office Action", U.S. Appl. No. 16/375,616, filed Apr. 4, 2019; dated Nov. 9, 2020.

Blaise, Malina, "Non-Final Office Action", U.S. Appl. No. 16/375,616, filed Apr. 4, 2019; dated May 19, 2020.

Cushner, Keith, "Top Sleep Apps", Published Feb. 24, 2021; https://www.tuck.com/sleep/best-sleep-apps/ ; Viewed online Apr. 20, 2021.

Dahl, Melissa, "Should I Buy This App That Says It Will Help Me Learn in My Sleep?", Published Oct. 7, 2015 online at https://www.thecut.com/2015/10/can-you-really-learn-while-you-sleep.html ; Viewed online Apr. 20, 2021.

Garfield, Leanna, "I spent a month trying to learn French in my sleep—here's what happened", Business Insider—Tech Review; Published Nov. 25, 2015; Viewed online Apr. 20, 2021 at https://www.businessinsider.com/do-sleep-learning-apps-work-2015-11.

Hindy, Joe, "10 Best Sleep Tracker Apps for Andriod", Published online Jun. 14, 2020; https://www.androidauthority.com/best-sleep-tracker-apps-android-789293/ ; Viewed online Apr. 20, 2021.

Holmes, Lindsay, "You Can Actually Learn New Information While You Sleep", HuffPost; Published online Aug. 11, 2017, Updated Oct. 23, 2017 at https://www.huffpost.com/entry/sleep-learning-study_n_598b4838e4b0d793738c2532 ; Viewed online Apr. 20, 2021.

Kleitman, Nathaniel, "Sleep and Wakefulness", Published 1939 by The University of Chicago Press; pp. 125 and 126; Viewed online at https://books.google.com/books?id=FwKzKM4sdEoC&pg=PA725&dq=%22sleep%20learning%22&authuser=0#v=onepage&q=%22sleep%20learning%22&f=false ; Apr. 20, 2021.

Sandoiu, Ana, "Can you learn in your sleep? Yes, and here's how", Published Mar. 8, 2018 online at https://www.medicalnewstoday.com/articles/321161 ; Viewed online Apr. 20, 2021.

Tacsik, Ernest, "Final Office Action", U.S. Appl. No. 16/375,646, filed April 4, 20219; dated May 21, 2021.

Tacsik, Ernest G., "NonFinal Office Action", U.S. Appl. No. 16/275,646, filed Feb. 13, 2020; dated Feb. 13, 2020.

Witkowski, et al., "Sleep-Learning Was a Myth, But you Could Strengthen Memories While you Snooze", Smithsonian Magazine; Published Feb. 16, 2018; https://www.smithsonianmag.com/science-nature/how-sound-and-smell-cues-can-enhance-learning-while-you-sleep-180968180/ ; Viewed online Apr. 20, 2021.

Blaise, Malina, "Final Office Action", U.S. Appl. No. 16/375,616, filed Apr. 4, 2019; dated Oct. 22, 2021.

* cited by examiner

USER STATE-BASED DEVICE POWER CONSERVATION

TECHNICAL FIELD

The present disclosure is related generally to mobile electronic communications devices and, more particularly, to systems and methods for managing device power use based on a physical state of a device user.

BACKGROUND

In recent years, mobile devices such as cell phones and smart phones have become increasingly integrated into their user's lives. Indeed, users tend to use their devices while exercising, travelling, playing and even sleeping. As to the latter, users frequently listen to audio programs or music while they are falling asleep. While this tends to aid users in falling asleep, device power may be needlessly consumed after the user has fallen asleep.

In addition, alerts and notifications by such a device may be wasted in the event the user is not awaken by them, or may be intrusive in the event the user is awakened by them. Moreover, for users attempting to learn material via their device, the reinforcement of such learning is much more efficacious at certain times and much less at other times, depending upon the user state.

Finally, while much research has been performed on the topic of battery and data optimization in small user devices, such tasks are still executed in a suboptimal fashion by failing to account for user state. That is, device power management as it currently exists may not accurately determine when a user is likely to use certain resources, thus resulting in wasted expenditure of time and power to acquire unneeded materials, or alternatively causing unwanted delay for the user by failing to timely acquire needed materials.

Before proceeding to the remainder of this disclosure, it should be appreciated that the disclosure may address some or all of the shortcomings listed or implicit in this Background section. However, any such benefit is not a limitation on the scope of the disclosed principles, or of the attached claims, except to the extent expressly noted in the claims.

It should also be appreciated that the discussion of technology in this Background section is reflective of the inventors' own observations, considerations, and thoughts, and is in no way intended to be, to accurately catalog, or to comprehensively summarize any prior art reference or practice. As such, the inventors expressly disclaim this section as admitted or assumed prior art. Moreover, the identification or implication herein of one or more desirable courses of action reflects the inventors' own observations and ideas, and should not be assumed to indicate an art-recognized desirability.

BRIEF DESCRIPTION OF THE SEVERAL VIEWS OF THE DRAWINGS

While the appended claims set forth the features of the present techniques with particularity, these techniques, together with their objectives and advantages, may be best understood from the following detailed description taken in conjunction with the accompanying drawings of which:

DETAILED DESCRIPTION

Figure 1:
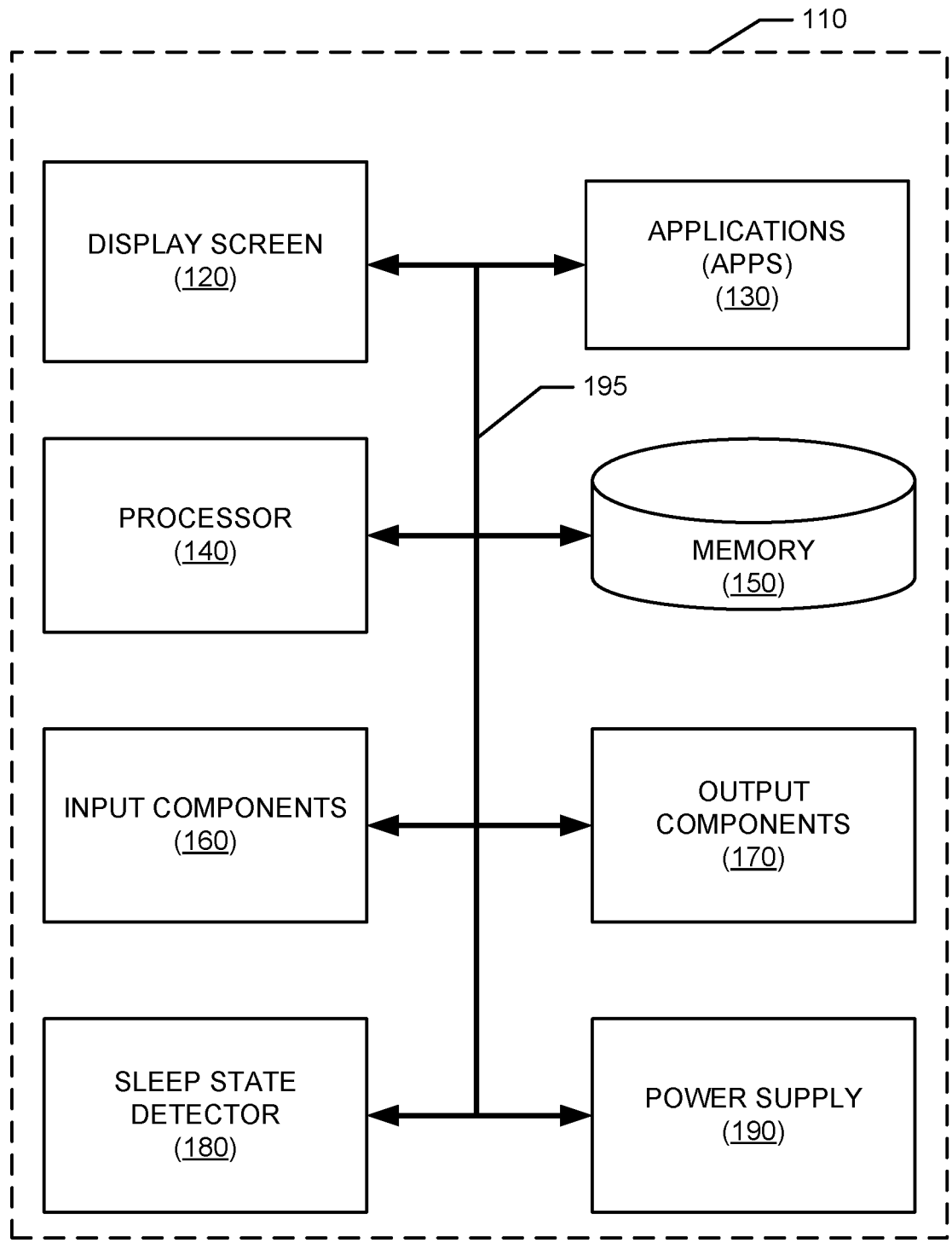
FIG. 1 is a schematic representation of a mobile electronic device in which various embodiments of the disclosed principles may be implemented.

Before discussing embodiments of the disclosed principles in full detail, an overview of certain embodiments is given to aid the reader in understanding the later more detailed discussion. As noted above, mobile devices such as cell phones and smart phones may be used by their users to aid in falling asleep, e.g., by playing audio programming, music, and so on. However, the use of devices in this way may result in the waste of device electrical power resources after the user has fallen asleep.

In an embodiment of the disclosed principles, the user device is constructed and configured to conserve resources once the user has fallen into a deep sleep state by turning off any music or other audio material that is being played. In an embodiment, visual materials such as movies or videos are also turned off at this time.

Similarly, alerts and notifications by such a device may be needlessly issued if the user is not awakened by them. Similarly, these same noises may be considered intrusive if they awaken the user from sleep. As such, in an embodiment of the disclosed principles, the user device is constructed and configured to hold any such alerts and notifications when the user has entered a deep sleep state.

For learning applications of the mobile device, the execution and reinforcement of such learning is much more efficacious at certain times and much less at other times, depending upon the user state. For example, a user in a light sleep state is reasonably receptive to audio learning reinforcement, while a user in a deep sleep state is not. As such, in an embodiment of the disclosed principles, the user device is constructed and configured to turn off audio learning material when the user of the device enters a deep sleep state. Learning reinforcements may relate to any material that the user wants to learn, experience or memorize, e.g., languages, affirmations, exam material, hypnosis, chants, mantras and so on.

Finally, as noted above battery and data optimization are implemented inefficiently in many small user devices by failing to account for user state. However, in an embodiment of the disclosed principles, the user device is constructed and configured to delay all user-centric data retrieval while the user of the device is in a deep sleep state. User-centric data is data that it intended to be viewed or heard by the user. This means, for example, that emails and voice mails may not be retrieved during the user's deep sleep state. However, software updates and other non-user-centric data may be retrieved at this time.

With this overview in mind, and turning now to a more detailed discussion in conjunction with the attached figures, the techniques of the present disclosure are illustrated as being implemented in or via a suitable device environment. The following device description is based on embodiments and examples within which or via which the disclosed principles may be implemented, and should not be taken as limiting the claims with regard to alternative embodiments that are not explicitly described herein.

Thus, for example, while FIG. 1 illustrates an example mobile electronic communications device with respect to which embodiments of the disclosed principles may be implemented, it will be appreciated that other device types may be used, including but not limited to laptop computers, tablet computers, and so on. It will be appreciated that additional or alternative components may be used in a given implementation depending upon user preference, component availability, price point and other considerations.

In the illustrated embodiment, the components of the user device 110 include a display screen 120, applications (e.g., programs) 130, a processor 140, a memory 150, one or more input components 160 such as RF input facilities or wired input facilities, including, for example, one or more antennas and associated circuitry and logic. The antennas and associated circuitry may support any number of protocols, e.g., WIFI, BLUETOOTH, cellular, etc.

The device 110 as illustrated also includes one or more output components 170 such as RF (radio frequency) or wired output facilities. The RF output facilities may similarly support any number of protocols, e.g., WIFI, BLUETOOTH, cellular, etc., and may be the same as or overlapping with the associated input facilities. It will be appreciated that a single physical input may serve for both transmission and receipt.

The processor 140 can be a microprocessor, microcomputer, application-specific integrated circuit, or other suitable integrated circuit. For example, the processor 140 can be implemented via one or more microprocessors or controllers from any desired family or manufacturer. Similarly, the memory 150 is a nontransitory media that may (but need not) reside on the same integrated circuit as the processor 140. Additionally or alternatively, the memory 150 may be accessed via a network, e.g., via cloud-based storage. The memory 150 may include a random access memory (i.e., Synchronous Dynamic Random Access Memory (SDRAM), Dynamic Random Access Memory (DRAM), RAMBUS Dynamic Random Access Memory (RDRM) or any other type of random access memory device or system). Additionally or alternatively, the memory 150 may include a read-only memory (i.e., a hard drive, flash memory or any other desired type of memory device).

The information that is stored by the memory 150 can include program code (e.g., applications 130) associated with one or more operating systems or applications as well as informational data, e.g., program parameters, process data, etc. The operating system and applications are typically implemented via executable instructions stored in a non-transitory computer readable medium (e.g., memory 150) to control basic functions of the electronic device 110. Such functions may include, for example, interaction among various internal components and storage and retrieval of applications and data to and from the memory 150.

Further with respect to the applications and modules, these typically utilize the operating system to provide more specific functionality, such as file system service and handling of protected and unprotected data stored in the memory 150. In an embodiment, modules are software agents that include or interact with hardware components such as one or more sensors, and that manage the device 110's operations and interactions with respect to the described embodiments. In an embodiment, a sleep state detector 180 working in conjunction with associated sleep state sensors provides user sleep state information for use in the processes described herein.

With respect to informational data, e.g., program parameters and process data, this non-executable information can be referenced, manipulated, or written by the operating system or an application. Such informational data can include, for example, data that are preprogrammed into the device during manufacture, data that are created by the device or added by the user, or any of a variety of types of information that are uploaded to, downloaded from, or otherwise accessed at servers or other devices with which the device is in communication during its ongoing operation.

In an embodiment, a power supply 190, such as a battery or fuel cell, is included for providing power to the device 110 and its components. Additionally or alternatively, the device 110 may be externally powered, e.g., by a vehicle battery, wall socket or other power source. In the illustrated example, all or some of the internal components communicate with one another by way of one or more shared or dedicated internal communication links 195, such as an internal bus.

In an embodiment, the device 110 is programmed such that the processor 140 and memory 150 interact with the other components of the device 110 to perform a variety of functions. The processor 140 may include or implement various modules and execute programs for initiating different activities such as launching an application, transferring data and toggling through various graphical user interface objects (e.g., toggling through various display icons that are linked to executable applications).

Figure 2:
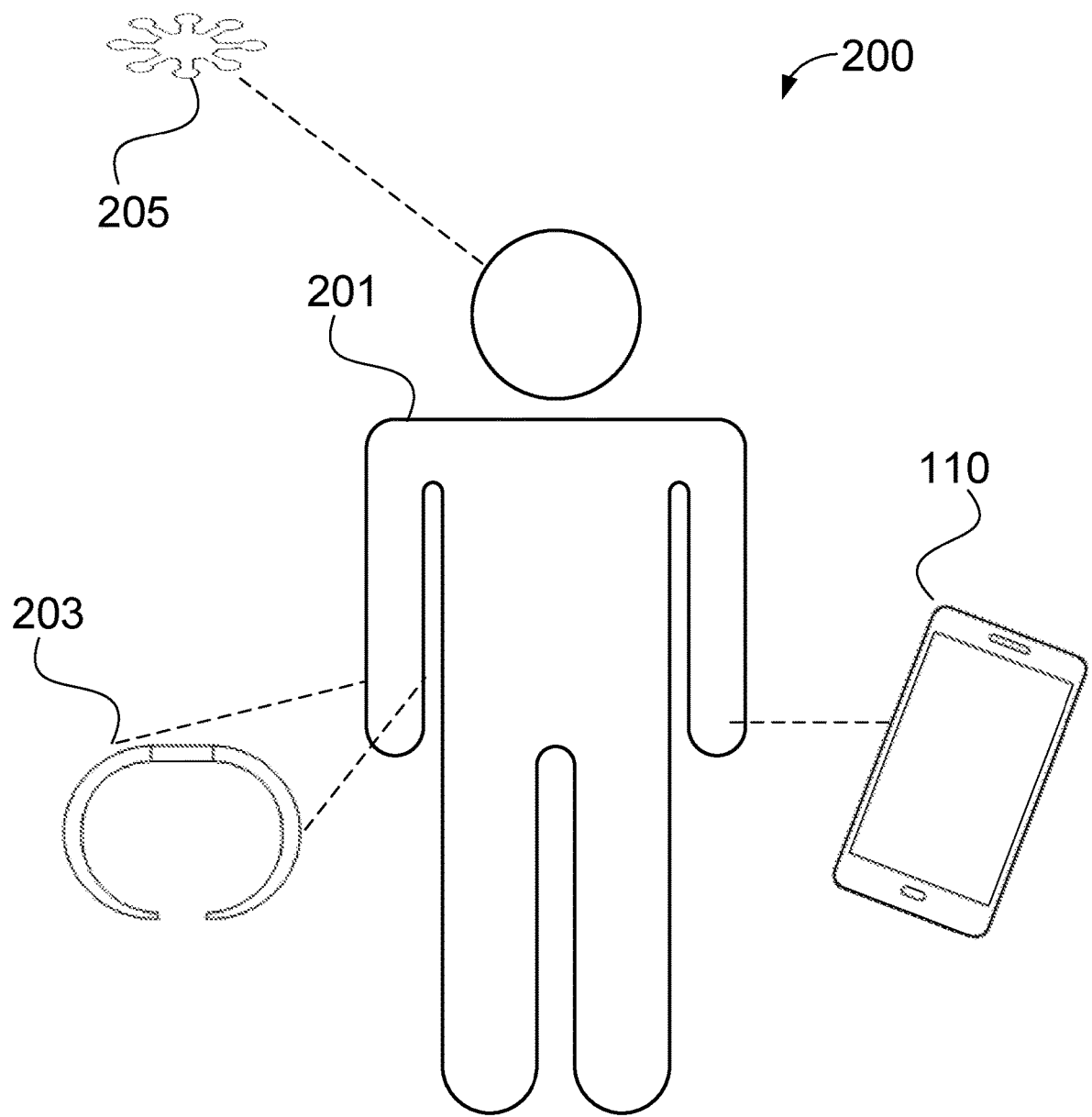
FIG. 2 is a simplified schematic diagram showing a usage environment within which the described embodiments may be implemented.

FIG. 2 is a simplified schematic diagram showing a usage environment within which the described embodiments may be implemented. As shown, the example environment 200 includes a mobile device 110 associated with a user 201 as well as a sleep-state sensor device 203 associated with the user 201. The sleep-state sensor device 203 may be worn by the user 201, placed on the user 201, in a non-contact relationship with the user 201 or otherwise positioned and configured to gather data associated with the user's sleep state. The sleep-state sensor device 203 may also be linked, e.g., wirelessly or otherwise, to the sleep state detector 180 (FIG. 1) within the device 110.

The user's sleep state may be one of awake, pre-deep sleep, deep sleep and post-deep sleep. The sleep-state sensor device 203 detects one or more of the user's breathing characteristics, heart rate, physical movement, physical movement frequency or duty cycle, micro-motion profile combined with other background context such as time, noise, voice and light. The collected data can then be used by the sleep-state sensor device 203 or the sleep state detector 180 (FIG. 1) to differentiate between deep sleep and the pre- or post-deep sleep states.

In an embodiment, the device 110 incorporates the sleep-state sensor device 203 in the form of a camera which can be used to differentiate between the deep sleep and pre- or post-deep sleep states by monitoring user facial features (e.g., movements of the eyelid or mouth), body motions, body position, body posture and chest movement. The device 110 microphone may also be used to provide audio detection of sleep state indicators.

In a further embodiment, more accurate sleep state data is provided by the sleep-state sensor device 203 via brain wave sensing, e.g., via EEG. A stretchable wearable cap or net 205 in this embodiment couples the waves in the scalp area to electrical contacts (e.g., on or behind the ear). The signals thus captured are then amplified by the sleep-state sensor device 203 and assessed for user alertness level.

Although those of skill in the art are aware of how brainwave activity is correlated to sleep state, we will provide a brief discussion for those of more casual familiarity with the art. Brain waves may be characterized as one of beta waves, alpha waves, theta waves and delta waves. Of these, the presence of beta waves indicates that the subject is awake and alert, while the presence of alpha waves indicates that the subject is awake but is relaxed or reflective.

The presence of theta waves indicates that the subject is drowsy, while the presence of delta waves indicates that the subject is sleeping. Delta waves can indicate either light sleep or deep sleep, and are thus labelled as either NREM (non-rapid eye movement) delta waves for light sleep or REM (rapid eye movement) delta waves for deep sleep.

This delineation can be made based upon the activity within the delta wave form. Brain waves during REM sleep (deep sleep) occur after NREM delta waves occur and are of lower amplitude and higher frequency range than either theta waves or NREM delta waves.

Once the user's status is determined, whether the user's state is determined via brain wave measurements or other physical observations, a number of actions are taken based on the user state.

In an embodiment of the disclosed principles, the user's state is used to time alerts and notifications. For example, if the user is alert and active, then actions or activities which might be alarming if the user were asleep are not alarming. However, if the user's children are engaged in a project or activity that requires parental supervision, for example, and the user is sensed going from alert to pre-sleep, then the device may provide alerts that must be given prior to sleep. In the foregoing example, such an alert would alert the user, prior to sleep, that the project under supervision is still ongoing.

Other example alerts that would be issued pre-sleep include an alert that the user's children are in the yard alone, an alert that pets are out, an alert to shut the garage door, an alert to lock the car, an alert to take medication before falling asleep, alerts for early tasks the next day (by accessing the user's calendar), an alert to shut a sprinkler system off or an alert to turn off gas burners or any such household appliances.

With respect to media play, type and volume, the device may change a music volume or music type as the user transitions between alert and pre-sleep for example. Such actions are based on user history in an embodiment of the disclosed principles, wherein the user has previously lowered volume or changed media instance or type prior to sleep. Furthermore, the device may cease music play as soon as user enters into the deep sleep state. With respect to learning or knowledge reinforcement, the device is configured to play such materials when the user is asleep but receptive, that is, during pre-deep sleep.

As noted above, the device 110 is also configured to handle calls and alerts that arise when the user is at one of the stages of sleep, i.e., REM sleep or NREM sleep. In an embodiment, when user is in deep sleep, the device silences alerts and automatically responds to incoming calls by indicating that the user is not available. In an embodiment, the device 110 selects one of multiple voicemail prompts, wherein the prompt is selected based on the identity or class of the caller. Thus, for example, when the caller is a family member, the device may select a prompt indicating that the user is sleeping, whereas when the caller is a non-family, the device may select a prompt simply indicating that the user is unavailable. Further, the device may select different prompts to present to favorite contacts as opposed to non-favorite contacts.

However, if the same caller calls again within a short time interval (repeat call window), the device awakens the user, e.g., via gradually louder rings that increase in volume until the user answers or maximum volume is reached. Alternatively, the device may issue an emergency ring tone that differs from the user's usual ring tones. In an embodiment of the described principles, second call handling as above is only performed when the caller is in the user's contacts saved with respect to the device 110. This allows the device 110 to avoid awaking the user from deep sleep to take unwanted but persistent calls, e.g., spam calls.

The device 110 may also control room lighting in response to the user's sleep state. For example, upon sensing that the user has entered deep sleep, the device 110 may turn off room lights, turns off a TV in the room, and may notify others (spouse, children) that the user is asleep.

With respect to the handling of alarms and reminders if the user has explicitly set an alarm or a reminder, the device may adjust the volume of the alarm or reminder depending on the user's sleep state. For example, at the time of the alarm or reminder, the device 110 may gradually increase the volume to maximum if the user is in deep sleep, to thus ensure that the user does not miss the alarm or reminder. In an optional embodiment, the alarms and reminders are repeated to the users during the pre-deep sleep state. In this way, the user's subconscious mind may internalize the alarm or reminder and be able to wake up at the set time or later recall the reminder.

When the user returns from sleep to the alert state, the device may execute one or more of a number of actions. For example, the device may list or otherwise summarize actions taken by the device while the user was in sleep or deep sleep, e.g., reminders initiated, calls handled, the state of associated IOT (internet of things) devices for user review and learning, and so on.

In an embodiment, the device 110 also controls its own mode, e.g., idle mode, doze mode or standby mode, based on the user's sleep state. For example, for efficient battery usage the device may enter an idle mode when the user enters deep sleep. In this mode, CPU and network activities will be restricted such that background data operations like email sync, and other media sync (e.g., news) and social networking updates will not be performed.

However, when the user subsequently moves from deep sleep mode to light sleep, the device may return to an operative mode such as standby, and execute activities that have been skipped during the device's idle mode. If the device 110 waited until the user awoke fully to begin data sync, there may be a delay when the user accesses the device upon awakening.

The following process descriptions will assume a user device similar to that of FIG. 1, but it will be appreciated that other device types and configurations may alternatively be used. As one non-limiting example, the user device may incorporate the sleep-state sensor device 203, and the functions of the sleep state detector 180 may be performed within or as part of another routine operating on the device 110.

Figure 3:
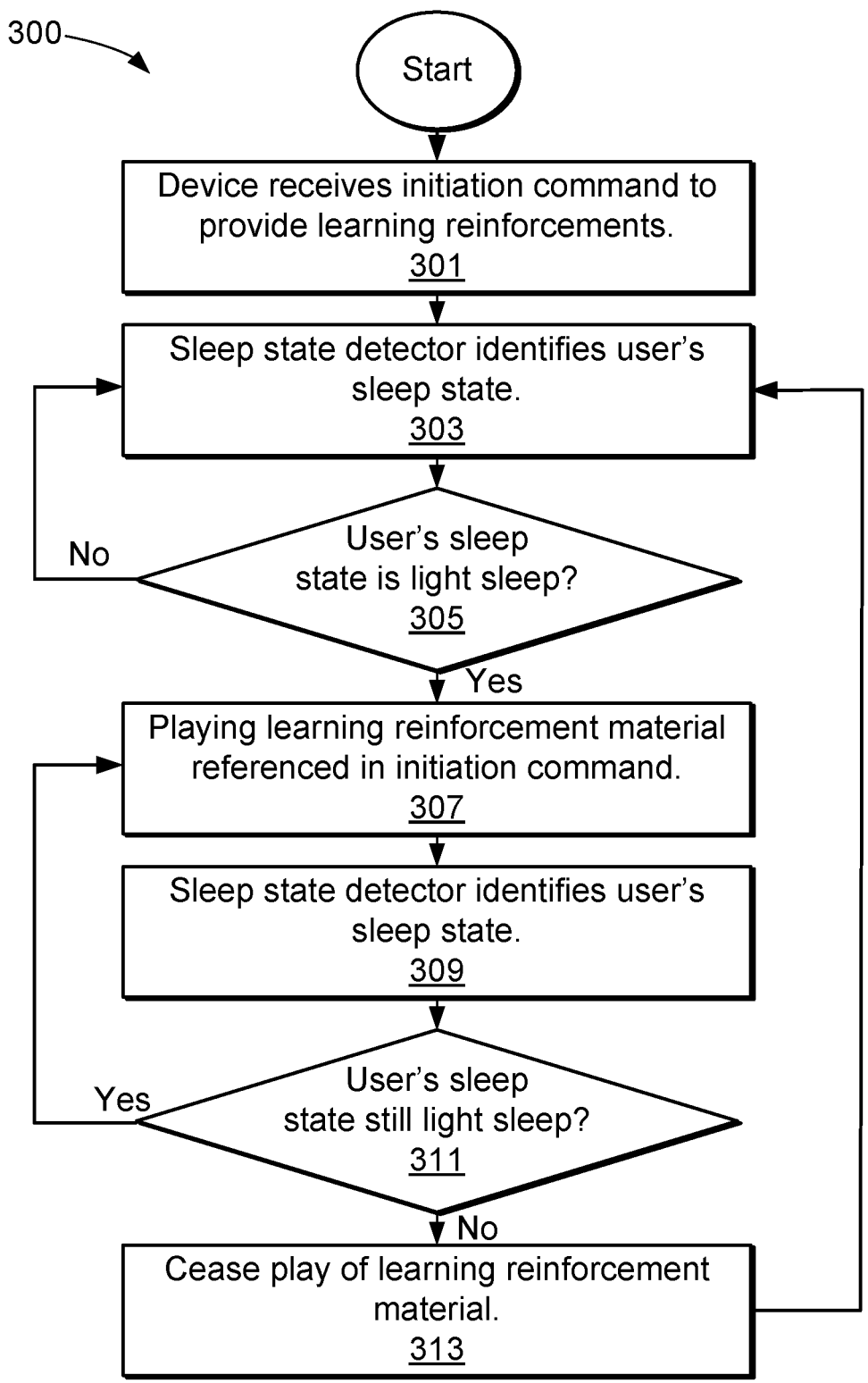
FIG. 3 is a flow chart of a process for providing learning reinforcements based on user sleep state in accordance with an embodiment of the disclosed principles.

Turning to FIG. 3, this figure provides a flow chart of a process for providing learning reinforcements based on user sleep state in accordance with an embodiment of the disclosed principles. In particular, in this example, the user device 110 provides a learning reinforcement function at a time when the user is most receptive to it, which is determined based on user sleep state.

Thus, at stage 301 of the process 300, the device 110 receives an initiation command to provide learning reinforcements. This initiation command may be the result of a timer or schedule or may result from a direct user command. The learning reinforcements will typically comprise audio material intended for memorization or internalization. At stage 303, the sleep state detector 180 of the user device 110 identifies the user's sleep state via the sleep-state sensor device 203. As noted above, the user's sleep state will be one of alert, drowsy, light sleep and deep sleep.

At stage 305, the sleep state detector 180 determines whether the user's current sleep state is light sleep, also referred to as pre-deep sleep or NREM deep sleep. If it is determined at stage 305 that the user's sleep state is light sleep, the process 300 moves forward to stage 307. Otherwise the process 300 returns to stage 303.

Moving to stage 307, it is at this stage that the sleep state detector 180 triggers the playing of the learning reinforcement material referenced in the initiation command received at stage 301. With the learning reinforcement material playing, the sleep state detector 180 once again identifies the user's sleep state via the sleep-state sensor device 203 at stage 309. The sleep state detector 180 then determines at stage 311 whether the user's current sleep state is still light sleep. If the user's sleep state is still light sleep, the process 300 loops back to stage 307. Otherwise, the process 300 moves forward to stage 313, turning off the play of the learning reinforcement material. From stage 313, the process 300 returns to stage 303 to check the user's sleep state until it is once again light sleep.

In this way, the learning reinforcement material is played to the user when it is most beneficial to do so. By so doing, the device not only conserves device power but also ensures the user does not miss any of the learning reinforcement material by having it played during a non-receptive period.

Figure 4:
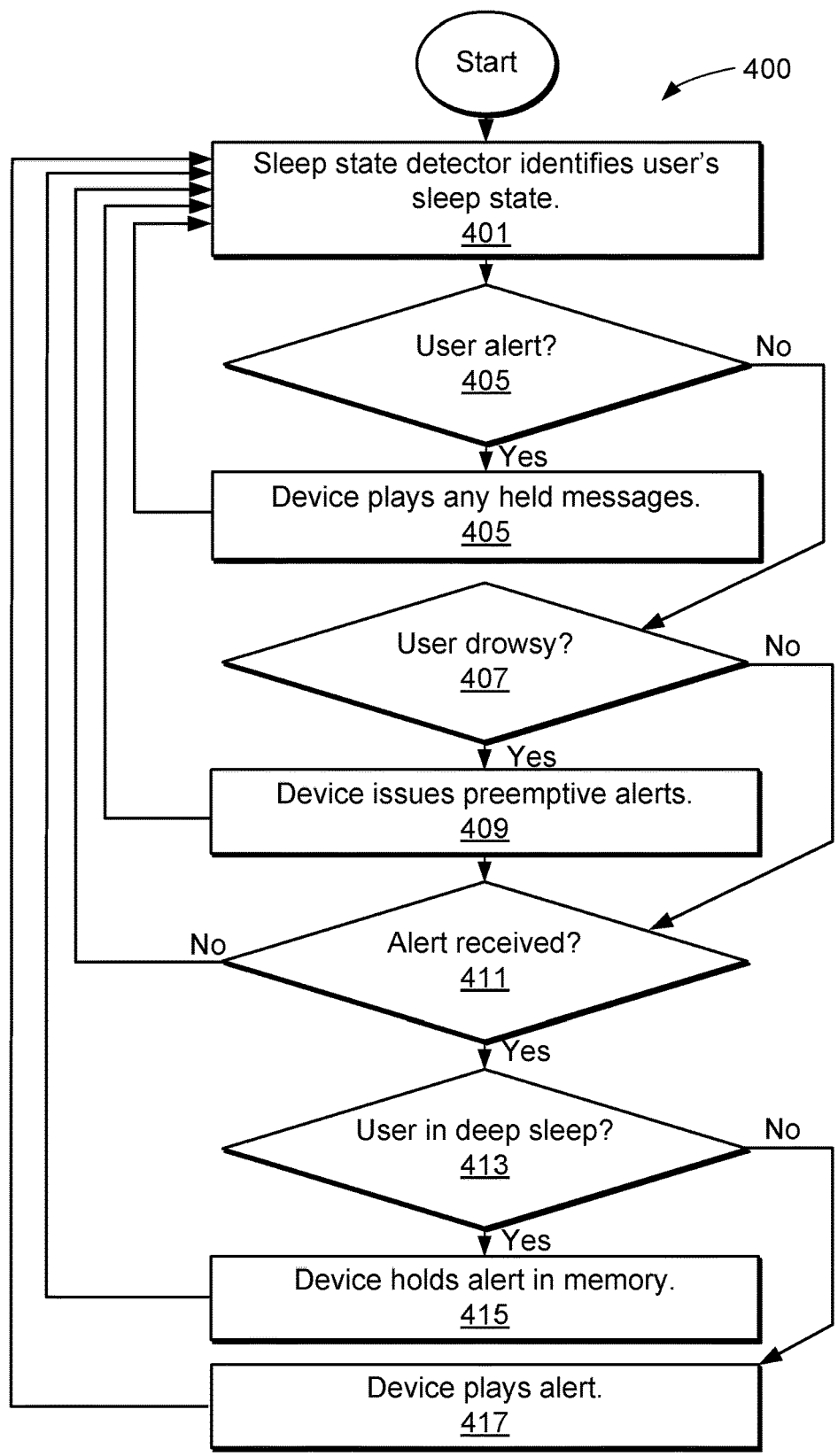
FIG. 4 is a flow chart of a process for handling device alerts based on sleep state in accordance with an embodiment of the disclosed principles.

Turning to FIG. 4, this figure provides a flow chart of a process for handling device alerts based on sleep state in accordance with an embodiment of the disclosed principles. As with the discussion of FIG. 3, this discussion assumes a user device similar to the user device 110 of FIG. 1, although any other suitable device and arrangement of components may be used.

Throughout the process 400, the device 110, and in particular the sleep-state sensor device 203, is aware of the user sleep state via the sleep state detector 180 (FIG. 1). The illustrated process 400 begins at stage 401, wherein the device 110 detects the user's sleep state. At stage 403, the device then determines whether the user is alert. If the user is alert, the device then plays any held messages at stage 405 and returns to stage 401. If the user is not alert, the process 400 moves to stage 407, wherein the device 110 determines whether the user is drowsy (e.g., if the user is evidencing theta wave brain activity).

If the user is determined at stage 407 to be drowsy, the process 400 moves to stage 409 wherein the device gives any known preemptive alerts and then returns to stage 401. These alerts are those that should be sent prior to the user falling asleep, e.g., an alert that the user's children are still outside, that the garage door is open, that the stove on, that the user has an early next day appointments and so on.

If the user is determined at stage 407 not to be drowsy, the process 400 moves to stage 411, wherein the device determines whether an incoming alert has been received. If no such alert has been received, the process returns to stage 401. Otherwise, the process moves to stage 413, wherein the device determines whether the user is in deep sleep. If it is determined that the user is in deep sleep, the process moves to stage 415, wherein the device holds alert in memory and returns to stage 401. If instead it is determined at stage 413 that the user is not in deep, the process moves to stage 417, wherein the device plays the alert and returns to stage 401.

Through this process 400, the device is able to minimize user disruption and ensure alert receipt by waiting until the user exits deep sleep, and then providing those delayed alerts when the user is able to hear them and will not be shaken from deep sleep.

Figure 5:
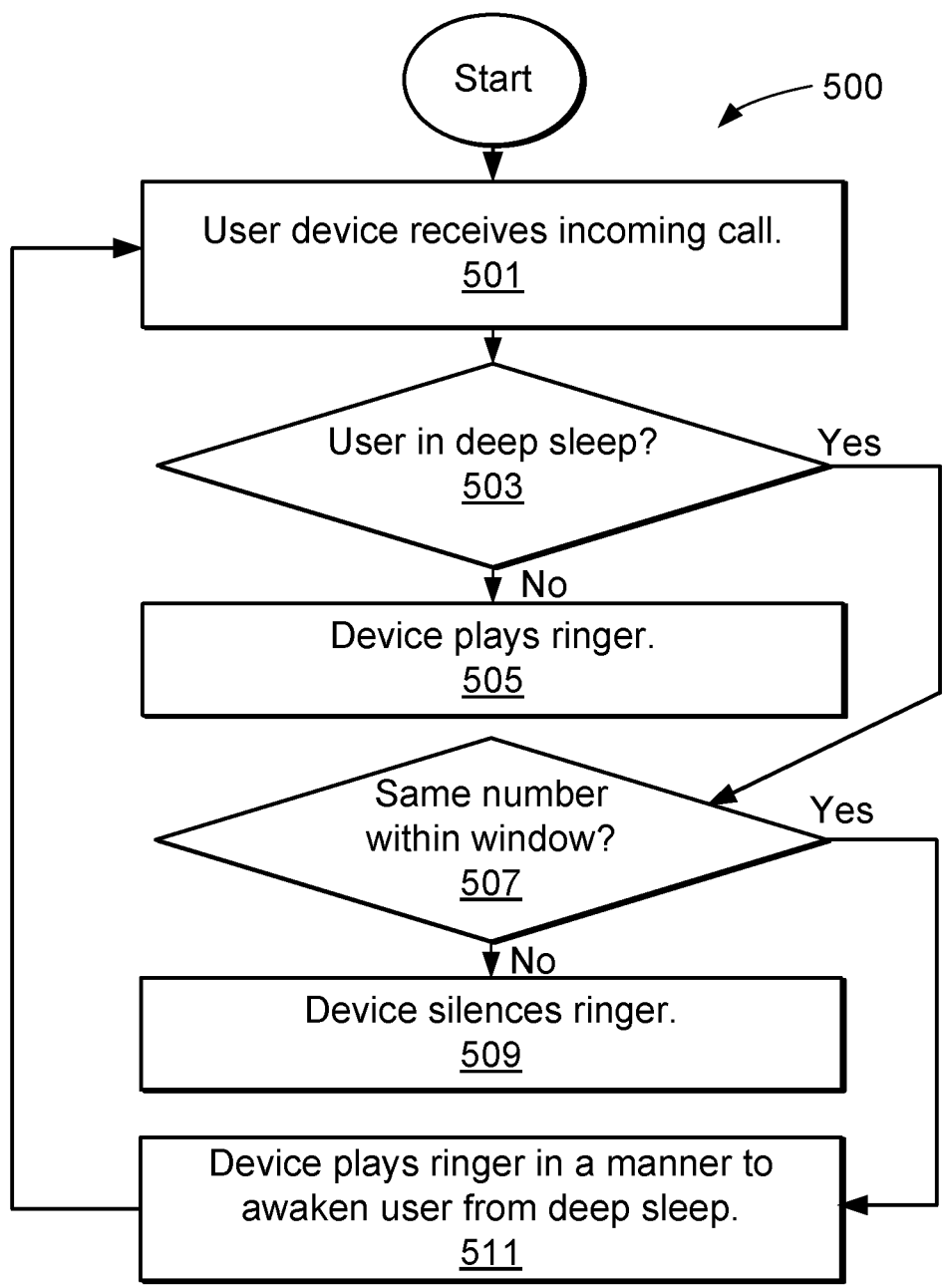
FIG. 5 is a flow chart of a process for handling incoming calls based on sleep state in accordance with an embodiment of the disclosed principles.

Turning to FIG. 5, this figure provides a flow chart of a process for handling incoming calls based on sleep state in accordance with an embodiment of the disclosed principles. At stage 501 of the illustrated process 500, the user device receives a phone call. At stage 503, the device determines whether the user is in a deep sleep state. If the user is not in a deep sleep state, the device rings the call ringer at stage 505. However, if the user is in a deep sleep state, the process moves to stage 507, wherein it is determined whether the received call is (a) from the same number as a previous call and (b) the call has been received with a predetermined second call window, e.g., 2 minutes or other suitable period.

If there was no prior call or the current call is either not from the same number as the prior call or not received within the predetermined second call window, then at stage 509, the device silences the device ringer. The device may optionally also provide a voicemail response to the caller at this stage, e.g., indicating that the user is unavailable and requesting that the caller leave a message.

If, however, it is determined at stage 507 that there was a prior call and that the current call is from the same number as the prior call and is received within the predetermined second call window, then at stage 511, the device rings the device ringer to awaken the user. The device may optionally ring the ringer in a progressively louder fashion to ensure that the user is awakened hut without unduly alarming the user. The process then returns to stage 501.

In an alternative or additional embodiment, the status of a call as urgent may be determined based on an area code of the caller. For example, if the call originates from an area code where the current time is unusual for a call, such as between midnight and 5 in the morning, then the device, in this optional embodiment, will designate the call as urgent. As such, it will treat the call as it would treat a call that occurred twice within the second call window.

In a further embodiment, the urgency of the call is determined based at least in part on the identity or class of the caller. Thus, for example, if the caller is a family member, the very fact that a call from family is occurring during a predetermined late call window is sufficient to label the call urgent and awake the user. Similarly, calls from favorited contacts may be treated as more likely to be urgent than calls from non-favorite contacts. This urgency level can be reflected in an enlargement of the second call window or by treating the first call from a favorited contact as urgent and awakening the user.

Figure 6:
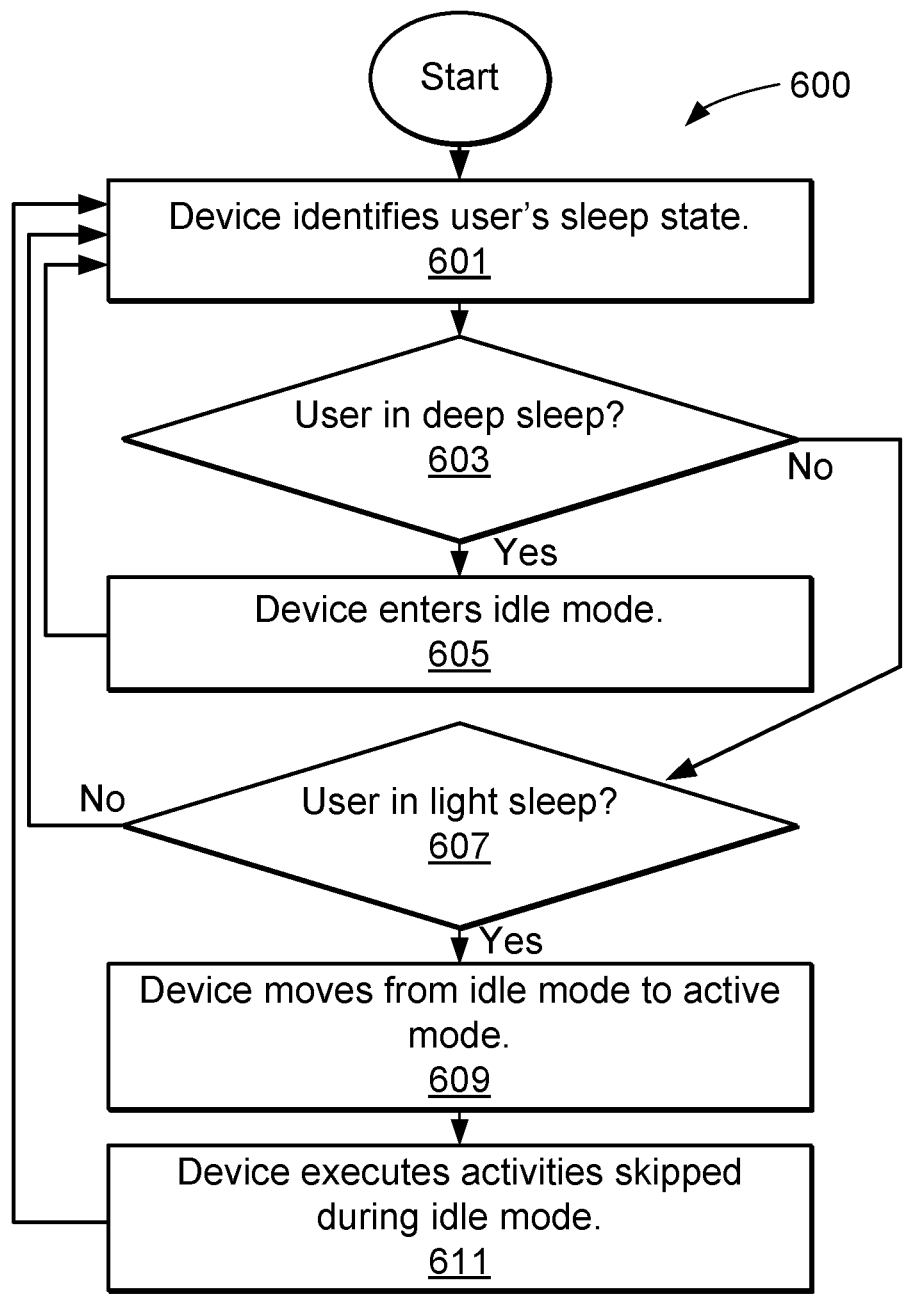
FIG. 6 is a flow chart of a process for sleep state-based battery and data optimization in accordance with an embodiment of the disclosed principles.

As noted above, a sleep state determination can also be used to enhance data and power efficiency in a user device such as the device 110 of FIG. 1 or similar device. Turning now to FIG. 6, this figure provides a flow chart of a process for sleep state-based battery and data optimization in accordance with an embodiment of the disclosed principles. At stage 601 of the process 600, the device 110 detects the sleep state of the device user. As noted above, this may be accomplished by the sleep state detector 180 of the user device 110 via the sleep-state sensor device 203.

If the user is determined at stage 603 to be in deep sleep, then the process 600 moves forward to stage 605 wherein the device 110 enters an idle mode. In the idle mode, CPU and network activities are restricted such that user-centric background data operations like email sync, media sync (e.g., news) and social networking updates will not be performed. User-centric data is data that it intended to be viewed or heard by the user. However, non-user-centric activities such as software updates, and backup and restoration of app data to app servers (e.g., backup of WHATSAPP data to WHATSAPP cloud or GOOGLE photos to GOOGLE cloud) may proceed during the idle mode. From stage 605, the process 600 returns to stage 601.

Continuing, in the event that the user was determined at stage 603 to not be in a deep sleep state, the process 600 moves to stage 607, wherein the device 110 determines whether the device user is in a light sleep state. If it is determined at stage 607 that the user is not in a light sleep state, then the process returns to stage 601. Otherwise, if it is determined at stage 607 that the user is in a light sleep state, the device 110 exits the idle mode at stage 609 to enter an operative state such as a standby mode, and executes any activities that have been skipped due to the device's idle mode at stage 611. From stage 611, the process 600 returns to stage 601.

It will be appreciated that various systems and processes have been disclosed herein. However, in view of the many possible embodiments to which the principles of the present disclosure may be applied, it should be recognized that the embodiments described herein with respect to the drawing figures are meant to be illustrative only and should not be taken as limiting the scope of the claims. Therefore, the techniques as described herein contemplate all such embodiments as may come within the scope of the following claims and equivalents thereof.

We claim:

1. A method of managing power and data usage in a mobile electronic communications device, the method comprising:
   detecting a sleep state of a user of the mobile electronic communications device, the sleep state being one of a light sleep state or a deep sleep state, by measuring brain waves of the user, the detecting comprising identifying the deep sleep state when measured brain waves are of a lower amplitude and within a higher frequency range than other brain waves measured during the light sleep state;
   entering an idle mode at the mobile electronic communications device when the sleep state of the user is the deep sleep state, wherein the idle mode restricts device CPU and network activities to exclude user-centric operations and silences alerts of incoming voice communications;
   receiving at least one incoming voice communication when the sleep state of the user is the deep sleep state;
   determining a class of caller making the at least one incoming voice communication when the sleep state of the user is the deep sleep state;
   transmitting a first voice mail prompt in response to the at least one incoming voice communication when the class of caller making the at least one incoming voice communication is a family member;
   transmitting a second voice mail prompt that is different from the first voice mail prompt in response to the at least one incoming voice communication when the class of caller making the at least one incoming voice communication is a non-family member;
   thereafter, detecting that the sleep state of the user has changed from the deep sleep state to the light sleep state; and
   exiting the idle mode at the mobile electronic communications device and entering an operative state and executing any pending user-centric operations in response to detecting that the sleep state of the user has changed from the deep sleep state to the light sleep state.

2. The method in accordance with claim 1, wherein first voice mail prompt indicates that the user is sleeping.

3. The method in accordance with claim 2, wherein the second voice mail prompt indicates that the user is unavailable.

4. The method in accordance with claim 1, wherein the user-centric operations exclude software updates and backup and restoration of app data to app servers.

5. The method in accordance with claim 1, further comprising:
   receiving, while the sleep state of the user is the deep sleep state, at least one other incoming voice communication when the sleep state of the user is the deep sleep state;
   identifying that a caller making the at least one other incoming voice communication also made the at least one incoming voice communication; and
   causing the mobile electronics communication device to emit an emergency ring tone while the sleep state of the user is the deep sleep state.

6. The method of claim 1, wherein the detecting the sleep state of the user of the mobile electronic communications device comprises:
   detecting the user experiencing non-rapid eye movement delta waves to determine the user is in the light sleep state; or
   detecting the user is experiencing rapid eye movement delta waves to determine the user is in the deep sleep state.

7. The method in accordance with claim 1, wherein the user-centric operations include at least one of email sync, media sync, and social networking update activities.

8. The method in accordance with claim 1, wherein the user-centric operations involve data to be presented to the user.

9. The method in accordance with claim 1, wherein the operative state is a standby mode.

10. The method in accordance with claim 1, wherein the user-centric operations require obtaining data to be presented to the user.

11. The method in accordance with claim 1, wherein the user-centric operations exclude software update operations and backup and restoration operations of application data.

12. A mobile electronic communications device with power and data management, the mobile electronic communications device comprising:
   a user interface facility comprising an audio speaker and a viewing screen; and
   a processor linked to the user interface facility and a sleep state sensor device, configured to:
      detect a sleep state of a user of the mobile electronic communications device from signals received from the sleep state sensor device measuring brain waves of the user, the sleep state being one of a light sleep state or a deep sleep state identified when measured brain waves are of a lower amplitude and within a higher frequency range than other brain waves measured during the light sleep state;

cause the mobile electronic communications device to enter an idle mode when the sleep state of the user is deep sleep, wherein the idle mode restricts device CPU and network activities to exclude user-centric operations and silences alerts of incoming voice communications;

receive at least one incoming voice communication when the sleep state of the user is the deep sleep state;

determine a class of caller making the at least one incoming voice communication when the sleep state of the user is the deep sleep state;

transmit a first voice mail prompt in response to the at least one incoming voice communication when the class of caller making the at least one incoming voice communication is a family member;

transmitting a second voice mail prompt that is different from the first voice mail prompt in response to the at least one incoming voice communication when the class of caller making the at least one incoming voice communication is a non-family member;

detect that the sleep state of the user has changed from a deep sleep state to a light sleep state; and cause the mobile electronic communications device to exit the idle mode in response to detecting that the sleep state of the user has changed from the deep sleep state to the light sleep state from the signals received from the sleep state sensor device, and enter an operative state, and, while in the operative state, execute any pending user-centric operations.

13. The mobile electronic communications device in accordance with claim 12, wherein the sleep state sensor device further differentiates between sleep states of the user by monitoring physical changes of the user combined with at least one background context.

14. The mobile electronic communications device in accordance with claim 13, wherein the physical changes of the user comprise a micro-motion profile of the user and the at least one background context comprises background noise.

15. The mobile electronic communications device in accordance with claim 12, wherein the sleep state sensor device further differentiates between sleep states of the user by monitoring a duty cycle of physical movement of the user.

16. The mobile electronic communications device in accordance with claim 15, the sleep state sensor device further comprising a microphone providing audio detection of indicators of the sleep states, wherein the processor is configured to differentiate the sleep states of the user of the mobile electronic communications device from a combination of the duty cycle of the physical movement of the user and the audio detection of the indicators of the sleep states.

17. The mobile electronic communication device of claim 12, further comprising the sleep state sensor device.

18. The mobile electronic communication device of claim 17, wherein the sleep state sensor device further detects breathing characteristics of the user, a heart rate of the user, physical movement of the user, a physical movement frequency of the user, time of day, background noise, a voice of the user, and background light.

19. The mobile electronic communication device of claim 12, the sleep state sensor device comprising a head-worn sleep state sensor device.

20. The mobile electronic communication device of claim 19, the sleep state sensor device comprising stretchable net or cap.

* * * * *